United States Patent
Claude

(10) Patent No.: US 11,944,806 B2
(45) Date of Patent: Apr. 2, 2024

(54) TRANSCRANIAL ALTERNATING CURRENT DYNAMIC FREQUENCY STIMULATION METHOD FOR ANXIETY, DEPRESSION, AND INSOMNIA (ADI)

(71) Applicant: Nexalin Technology, Inc., Houston, TX (US)

(72) Inventor: John Patrick Claude, Redwood City, CA (US)

(73) Assignee: NEXALIN TECHNOLOGY, INC., Houston, TX (US)

( * ) Notice: Subject to any disclaimer, the term of this patent is extended or adjusted under 35 U.S.C. 154(b) by 412 days.

(21) Appl. No.: 17/337,653

(22) Filed: Jun. 3, 2021

(65) Prior Publication Data

US 2022/0023615 A1  Jan. 27, 2022

Related U.S. Application Data

(60) Provisional application No. 63/054,955, filed on Jul. 22, 2020.

(51) Int. Cl.
*A61N 1/04* (2006.01)
*A61N 1/36* (2006.01)

(52) U.S. Cl.
CPC ....... *A61N 1/0456* (2013.01); *A61N 1/36025* (2013.01); *A61N 1/3603* (2017.08)

(58) Field of Classification Search
None
See application file for complete search history.

(56) References Cited

U.S. PATENT DOCUMENTS

| 5,540,736 A | 7/1996 | Haimovich |
| 6,904,322 B2 | 6/2005 | Katsnelson |

(Continued)

FOREIGN PATENT DOCUMENTS

| WO | WO2020041633 | 2/2020 |
| WO | WO2021102447 | 5/2021 |

OTHER PUBLICATIONS

Rodriquez, Kari; PCT International Search Report; dated Sep. 27, 2021; 9 pages; Alexandria, Virginia.

(Continued)

*Primary Examiner* — Michael W Kahelin
(74) *Attorney, Agent, or Firm* — STETINA BRUNDA GARRED & BRUCKER

(57) ABSTRACT

Electrostimulation systems and methods are contemplated in which a high current level, charge balanced alternating current electrical signal is generated for delivery to the frontal cortex region of a patient's brain. By stimulating this region of the brain with a charged balanced stimulation current with a stimulation current envelope defining one or more series of pulses at particular frequencies and durations designed to evoke metabolic response in the neurons, significant improvements in efficacy and reductions in patient discomfort may be achieved relative to earlier methods of transcranial electrical stimulation, especially those in which result in a resultant rectified direct current component being administered to the patient. Further advantages, especially in promoting neural entrainment, may be realized as well via utilizing multiple series of pulses at different frequencies, and via the dynamic adjustment of the stimulation waveform via incorporation of feedback signals in order to maintain charge balance in real-time.

8 Claims, 6 Drawing Sheets

(56) References Cited

U.S. PATENT DOCUMENTS

| | | |
|---|---|---|
| 7,742,823 B2 | 6/2010 | King et al. |
| 7,769,463 B2 | 8/2010 | Katsnelson |
| 9,227,056 B1 | 1/2016 | Heldman et al. |
| 2006/0015153 A1 | 1/2006 | Gliner et al. |
| 2008/0319492 A1 | 12/2008 | Katsnelson |
| 2009/0149898 A1 | 6/2009 | Hulvershorn et al. |
| 2012/0310298 A1 | 12/2012 | Besio et al. |
| 2015/0238759 A1 | 8/2015 | Katsnelson |
| 2015/0328467 A1 | 11/2015 | Demers et al. |
| 2016/0136427 A1* | 5/2016 | De Ridder ......... A61N 1/36139 607/45 |
| 2016/0175585 A1 | 6/2016 | Gregory et al. |
| 2016/0206883 A1 | 7/2016 | Bornzin et al. |
| 2016/0346530 A1 | 12/2016 | Jeffery et al. |
| 2017/0296121 A1 | 10/2017 | Dar et al. |
| 2019/0209841 A1 | 7/2019 | Errico et al. |
| 2020/0023189 A1 | 1/2020 | Gribetz et al. |
| 2020/0038656 A1 | 2/2020 | Tyler et al. |
| 2021/0038892 A1 | 2/2021 | Velasco Valcke |
| 2022/0160995 A1* | 5/2022 | Wetmore ............. A61M 21/00 |

OTHER PUBLICATIONS

Rodriquez, Kari; PCT International Search Report; dated Oct. 25, 2021; 18 pages; Alexandria, Virginia.

* cited by examiner

TRANSCRANIAL ALTERNATING CURRENT DYNAMIC FREQUENCY STIMULATION METHOD FOR ANXIETY, DEPRESSION, AND INSOMNIA (ADI)

CROSS-REFERENCE TO RELATED APPLICATIONS

This application relates to and claims the benefit of U.S. Provisional Application No. 63/054,955 filed Jul. 22, 2020 and entitled "TRANSCRANIAL ALTERNATING CURRENT DYNAMIC FREQUENCY STIMULATION (TACS) SYSTEM AND METHOD FOR ANXIETY, DEPRESSION, AND INSOMNIA (ADI)" the entire disclosure of which is hereby wholly incorporated by reference.

STATEMENT RE: FEDERALLY SPONSORED RESEARCH/DEVELOPMENT

Not Applicable

BACKGROUND

1. Technical Field

The present disclosure relates generally to the field of electrostimulation. More particularly, the present disclosure relates to improved systems and methods for electrostimulation for treating Anxiety, Depression, and Insomnia (ADI) and other related diseases.

2. Related Art

Electrostimulation devices for applying current to a patient through electrodes located on the head have been developed and used for a variety of purposes in the past, such as for producing analgesic effects, inducing sleep, and reducing or controlling migraine headaches. Often, such treatments are referred to as transcranial electrostimulation (tCES) or cranial electrostimulation (CES). Conventional tCES devices, although employed for a number of different purposes, may have severe drawbacks. For example, many conventional tCES devices utilize a direct current (DC) component in order to break down or lower the resistance of the skin and to allow the treatment current (which may a combination of direct and alternating current) to penetrate to the nervous system.

The presence of a DC component of a treatment current produced by a TCES device generally results in an unpleasant experience for a patient undergoing TCES therapy. In early TCES designs, the presence of the DC current invariably would result in intense pain or burns to the skin of the wearer, requiring the placement of thick conductive padding between the electrodes and the skin of the wearer in order to render the treatment bearable. Even in more recently developed TCES therapies in which the levels of DC current are limited, these limited amounts of DC current still often result in substantial user discomfort. Additionally, even when only an alternating current is applied to the skin, the layers of the skin generally result in a non-linear, complex impedance that invariably rectifies the AC signal and generates a DC component. This DC component depolarizes nociceptors in the skin, causing discomfort in the patient. If the DC-stimulated nociceptors are efferent to a trigeminal nerve branch in the head, the discomfort may be projected into the forehead region.

This patient discomfort resulting from DC rectification presents an upper limit on the amount of power that can be delivered even in an AC-only TCES therapy. Because of this upper limit on power, such conventional therapies are limited in their efficacy.

Transcutaneous electrical nerve stimulation (tENS) is another technique by which electrostimulation devices apply current to patients through electrodes. tENS devices use lower voltage electrical current to provide short-term, non-invasive pain relief by delivering electrical impulses through the skin in order to stimulate nerves in the area in which electrodes are placed. Typically, tENS therapy relies on lower voltage electrical currents compared to transcranial stimulation, which relies on deeper penetration, and as such pain due to the electrical current itself is not typically reported. The exact mechanism of action of TENS therapy is still a matter of debate. One theory is that the transcutaneous delivery of electrical current across the nerves causes overstimulation of the affected nerves, diminishing or eliminating the capability of the affected nerves to perceive pain, and effectively "masking" pain that would otherwise be perceived nerves in the stimulated region. Another theory is that the nerve stimulation caused by the application of tENS therapy stimulates the production of endorphins, which independently act to block pain.

Conventional tENS devices and tENS electrodes, however, have only typically been used to treat pain in regions such as the extremities or the lower back. tENS devices typically carry strong warnings against application in regions such as the head, shoulders, or neck.

Therefore, novel systems and methods for electrostimulation are desirable for treating Anxiety, Depression, and Insomnia.

BRIEF SUMMARY

To solve these and other problems, novel systems and methods for treating a patient for Anxiety, Depression, and Insomnia (ADI) are contemplated in which an electrostimulation system produces a dual symmetric charge balanced alternating current electrical signal for delivery to the frontal cortex region of a patient's brain. By stimulating the frontal cortex region of the brain with a charged balanced AC stimulation current having a stimulation current envelope defining a series of pulses having a particular frequency, with the stimulation current being delivered for a particular duration, together designed to evoke particular metabolic responses in the neurons, significant improvements in efficacy and reductions in patient discomfort may be achieved relative to earlier methods of electrical stimulation, especially those in which a direct current or a resultant rectified direct current component is administered to the patient. Further advantages, especially in promoting neural entrainment, may be realized as well via delivery of the charged-balanced stimulation current such that its envelope defines multiple series of pulses at different frequencies, and via the dynamic alteration of the stimulation current via incorporation of feedback signals in order to maintain charge balance in real-time, in order to maintain charge balance.

Electrostimulation systems for treating a patient for Anxiety, Depression, and Insomnia are contemplated which may comprise a carrier waveform generator, a stimulation current generator, and a patient cable. A stimulation current may be generated from an carrier waveform output from the carrier waveform generator, with the carrier waveform being an alternating current having a duty cycle ratio and a current amplitude ratio, the duty cycle ratio and the current amplitude ratio being selected such that each respective integration of the current amplitude between successive time instances at which the carrier waveform alternates polarity is substantially equivalent. The stimulation current may be subsequently conveyed to the frontal cortex region of the patient via the patient cable in combination with electrodes configured for delivery to the frontal cortex region.

The contemplated electrostimulation systems for treating a patient for anxiety, depression, and insomnia may further be configured to amplitude modulate the carrier waveform prior during the process of generating the stimulation current, such that the extremes of the stimulation current define a stimulation current envelope. The stimulation current envelope may further be amplitude modulated such that the stimulation current envelope defines a first series of pulses occurring at a first frequency. The frequency of the first series of pulses may be between 4 and 100 Hz.

The contemplated transcranial electrostimulation systems for treating a patient for anxiety, depression, and insomnia may further be configured to generate a stimulation current wherein the stimulation current envelope further defines a second series of pulses occurring at a second frequency. The second series of pulse may occur at a frequency selected between 4 and 100 Hz.

The contemplated electrostimulation systems for treating a patient for Anxiety, Depression, and Insomnia may further be configured such that the stimulation current is conveyed to the patient for a treatment duration, with the stimulation current defining a stimulation current envelope, the stimulation current envelope defining a first series of pulses that occur at a first frequency for the entire treatment duration which does not substantially vary, and defining a second series of pulses that occur at a second frequency that varies during the treatment duration. According to particular exemplary embodiments, the second frequency may vary in accordance with predefined frequency levels corresponding to different portions of the treatment duration. The treatment duration may be, for example, about an hour, with the different portion of the treatment duration being a first portion of the treatment duration, a second portion of the treatment duration, and the third portion of the treatment, each being about 20 minutes.

According to various further refinements of the contemplated transcranial electrostimulation systems, the stimulation current may be configured such that it defines a stimulation current envelope which itself defines a plurality of series of pulses, each respective one of the plurality of series of pulses occurring at a respective frequency. In even further refinements of the above concept, each of the plurality of series of pulses defined by the stimulation current envelopes has a frequency selected between 4 Hz and 100 Hz.

The electrostimulation systems for treating a patient for Anxiety, Depression, and Insomnia may further be configured such that the carrier waveform may have a frequency of about 100 KHz, such that the carrier waveform is a rectangular wave, or both.

According to various further refinements of the contemplated electrostimulation systems, the system(s) may further comprise one or more reference electrodes, the stimulation current being measured at the patient by the one or more reference electrodes and an electrode contact impedance being determined therefrom, and a controller in communication with the one or more reference electrodes, the controller adjusting, based upon the determined electrode contact impedance, one or more parameters of: the carrier waveform output from the waveform generator, the stimulation current output from the stimulation current generator, or combinations thereof.

Methods for treating a patient for anxiety, depression, and insomnia are also contemplated, with such methods comprising the steps of: (a) generating a carrier waveform, the carrier waveform being an alternating current having a duty cycle ratio and a current amplitude ratio, the first duty cycle ratio and the first current amplitude ratio being selected such that each respective integration of the current amplitude between successive time instances at which the first waveform alternates polarity is substantially equivalent; and generating a stimulation current from the carrier waveform via amplitude modulation the carrier waveform, the extremes of the stimulation current defining a stimulation current envelope, the stimulation current envelope defining a first series of pulses occurring at a first frequency; and (b) applying the stimulation current to the frontal cortex region of the brain of the patient. According to particular refinements of such methods, the first series of pulses may occur at a frequency between 4 Hz and 100 Hz.

The step of generating a stimulation current may, in additional embodiments, occur via amplitude modulating the carrier waveform such that the stimulation current envelope current further defines a second series of pulses occurring at a second frequency. The frequency of the second series of pulses may be selected from a frequency between 4 Hz and 100 Hz.

The above-described methods may also comprise applying the stimulation current to the frontal cortex region of the brain of a to a patient for a treatment duration, wherein the first series of pulses occur at a predefined frequency that does not substantially vary for the entire treatment duration, and wherein the second series of pulses occur at a second frequency that varies during the treatment duration. According to particular exemplary embodiments, the second frequency may vary in accordance with predefined frequency levels corresponding to different portions of the treatment duration. The treatment duration may be, for example, about an hour, with the different portion of the treatment duration being a first portion of the treatment duration, a second portion of the treatment duration, and the third portion of the treatment, each being about 20 minutes.

According to further refinements of the above-described methods, the step of generating the stimulation current may be performed via amplitude modulating the carrier waveform such that the stimulation current envelope defines a plurality of series of pulses, each respective one of the plurality of series of pulses occurring at a respective frequency. Such frequencies may be selected from between 4 Hz and 100 Hz. Further, it is contemplated that the carrier waveform may have a frequency of about 100 KHz, may be a rectangular wave, or both.

In further refinements of the above-described methods, additional steps may be included such as: measuring the stimulation current at the patient, determining of an electrode contact impedance therefrom, and based upon the determined electrode contact impedance, adjusting one or more of: the waveform output from the waveform generator, the stimulation current output from the stimulation current generator, or combinations thereof.

A method of generating a stimulation current for the treatment of anxiety, depression, and insomnia via delivery to the frontal cortex is also contemplated, with the method comprising generating a carrier waveform, the carrier waveform being a rectangular alternating current having a duty cycle ratio and a current amplitude ratio, the duty cycle ratio and the current amplitude ratio being selected such that each respective integration of the current amplitude between successive time instances at which the waveform alternates polarity is substantially equivalent, and amplitude modulating the carrier waveform to derive a stimulation current, the extreme of the stimulation current defining a stimulation current envelope, the stimulation current envelope defining a first series of pulses occurring at a first frequency, with the first frequency being between 4 Hz and 100 Hz.

DETAILED DESCRIPTION

According to various aspects of the present disclosure, new systems and methods for treatment of anxiety, depression, and insomnia via electrostimulation are contemplated in which a "symmetric" or charge balanced AC signal is delivered to the patient in a manner that permits higher levels of overall power to be transmitted more deeply into the brain without the limitations of the patent discomfort threshold, permitting evocation of nerves in the deep brain structures and enhancing treatment outcome. This increase in power may enhance treatment efficacy and response without any adverse clinical sequelae. By amplitude modulating the carrier waveform to incorporating a blend of multiple frequency patterns of the series of pulses defined by the stimulation current envelope into the treatment, such as a first frequency pattern at a constant frequency for an entire one hour treatment duration, and a second frequency pattern having a varying frequency, the blended frequency pattern of the stimulation current envelope may result in metabolic cleansing and regeneration in damaged neurons, which in particular may be seen to treat both the symptoms and underlying causes of as anxiety, depression, and insomnia (ADI).

Figure 1:
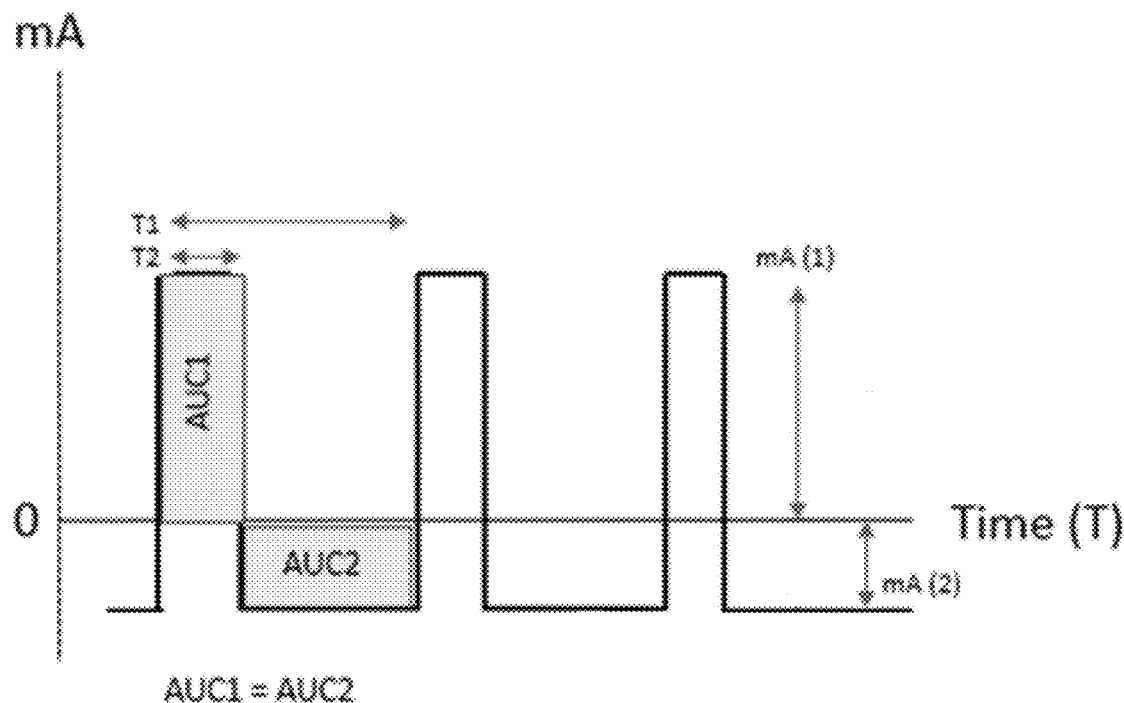
FIG. 1 is an illustration showing an embodiment of a high frequency (100 KHz) rectangular alternating current carrier waveform that is charge-balanced, in that the area under the curves (AUC) for each respective integration of current amplitude between successive time instances at which the carrier alternates polarity is equal, with such charge balance resulting from the choice of a particular duty cycle ratio (T2:T1) and a particular current amplitude ratio (Ma(1):Ma(2)) for the carrier waveform.

Turning now to FIG. 1, an exemplary embodiment of a rectangular alternating current (AC) carrier waveform is illustrated. As may be seen, the exemplary rectangular AC carrier waveform has, between each successive alternation of polarity, an area under the curve (AUC), i.e. the integration of the current amplitude between successive time instances at which the waveform alternates polarity. For the waveform to be "symmetric" or "change balanced," each successive pair of AUC between polarity shifts in the AC waveform must be equal. Via the original rectangular AC carrier waveform being charged balanced in this fashion, it may be seen that the ultimate stimulation current derived from amplitude modulating this waveform will not result in undesired rectification when applied to the patient's skin and thus will not result in the production of a DC component that will cause discomfort or pain in the patient.

The carrier waveform itself may be any type of alternating current waveform. In the exemplary embodiment of FIG. 1, it may be seen that the waveform is generally in the form of a rectangular wave. However, it may be seen that other waveform types may be used as carrier waveforms, such as sinusoidal or triangular waves. It may also be seen that this charge balancing, wherein the AUC of each successive pair of region between alternation in polarity are substantially equivalent, may be achieved in a variety of ways, such that each respective pair of waveforms is not necessarily required to have the same geometry as those preceding it. As shown in the image, the "on" positive amperage portions of the illustrated carrier waveform have a greater magnitude than the "off" negative amplitude portions, but are of a shorter duration (T2), with the duration of the "off" negative amperage portions of the carrier waveform being longer (T1-T2) and with a lesser magnitude. This ratio of the time when the carrier waveform "on" versus "off" is referred to as the duty cycle ratio, which is calculated here, when a rectangular AC waveform is used as the carrier wave, as (T2)/(T1). It may be seen that by controlling the relative magnitudes of the amperages, durations, and possibly even the shape itself of the carrier waveform or portions thereof (especially in non-square waveforms), a carrier waveform may be achieved that is charge balanced. Thus it may be seen that in the case of a dynamic signal, when the duty cycle ratio (T2/T1) of the waveform is changed, so must the current amplitude ratio (mA(1)/mA(2)) also be changed to compensate and maintain the charge balanced nature of the waveform in order to prevent the ultimate stimulation current produced from producing a rectified DC component at the patients' skin when applied to the patient. For example, with a rectangular waveform, the following Table 1 shows various duty cycles and corresponding carrier amplitude ratio pairings that will result in a charge balanced waveform:

TABLE 1

Charged Balanced Duty Cycle
Ratio and Current Amplitude Ratio Pairings

| Duty Cycle Ratio | Current Amplitude Ratio |
|---|---|
| 1:3 | 2:1 |
| 1:4 | 3:1 |
| 1:5 | 4:1 |

In the exemplary embodiment, the carrier waveform is a high-frequency rectangular alternating current, which has a frequency of about 100 KHz. It has generally been found that use high frequency carrier waveform is most beneficial for permitting deep penetration of the stimulation current into targeted regions of the patient's brain. However, in other embodiments, it is contemplated that higher or lower frequencies than 100 KHz may be utilized, without departing from the scope and spirt of the present disclosure. Likewise, it may also be seen that variation in the frequency of the carrier waveform over time or in response to stimuli or other inputs may be utilized in order to enhance the functionality of the transcranial electrostimulation device.

Figure 2:
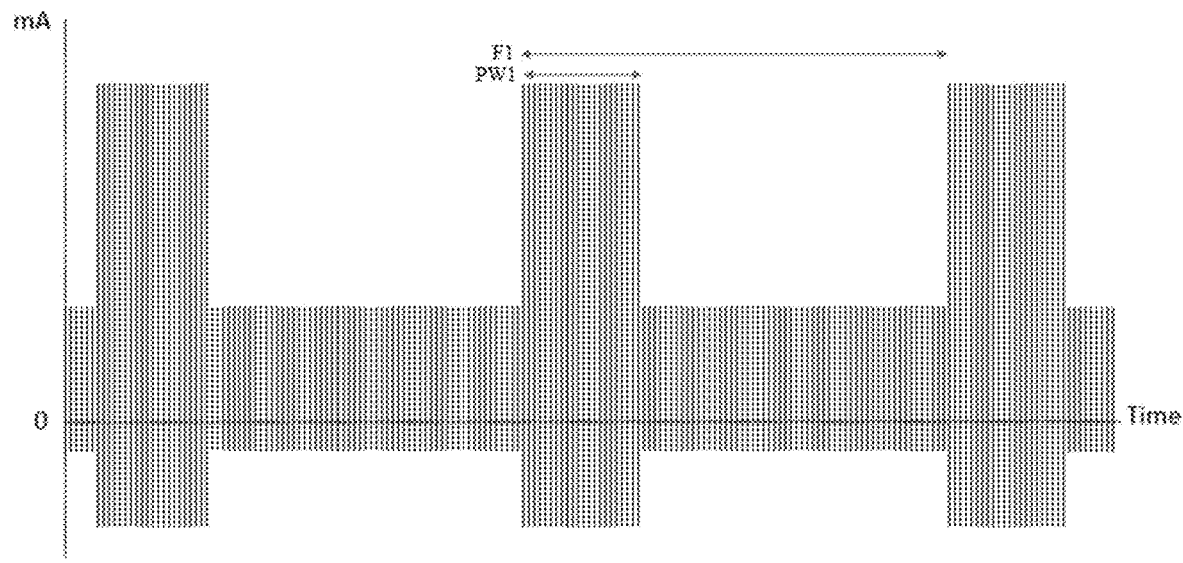
FIG. 2 is an illustration showing one embodiment of stimulation current comprising the result of amplitude modulating the carrier waveform of FIG. 1 such that the extremes of the stimulation current define a stimulation current envelope, with the stimulation current envelope defining a first series of pulses occurring at a frequency F1 and having a pulse width PW1.

Turning now to FIG. 2, an exemplary embodiment of a stimulation current that has been produced via amplitude modulation of the high frequency carrier waveform of FIG. 1 is illustrated. As may be seen, the extremes of the amplitude modulated high frequency carrier waveform define a stimulation current envelope, which results as a consequence of the particular parameters of the amplitude modulation. The stimulation current envelope may itself be seen to define a first series of pulses occurring at a first frequency F1 and having a pulse width PW2. When applied to the frontal cortex region of the patient's brain, the stimulation current may induce neural entrainment, causing neurons within the patient's brain to be stimulated via polarization of the electrical charge on the outside of the membrane in accordance with the frequency of the first series of pulses. As long as the magnitude and pulse width of the pulses defined by the stimulation current envelope are sufficient to promote neural stimulation and trigger an action potential, and as long as the frequency of the series of pulses are not too high so as to permit the neuron to complete its refractory period prior to excitation via the subsequent pulse, neural entrainment may occur at the neurons that are affected by the stimulation current.

Figure 3:
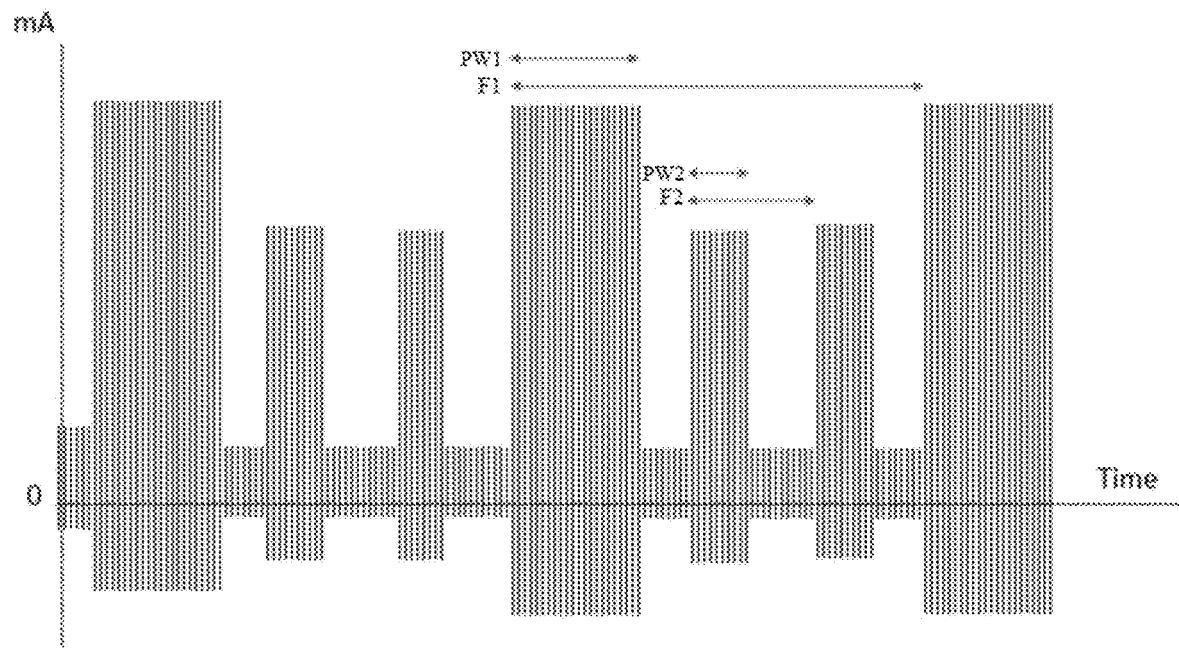
FIG. 3 is an illustration showing another embodiment of a stimulation current comprising the result of amplitude modulating the carrier waveform of FIG. 1 such that the extremes of the stimulation current define a stimulation current envelope, with the stimulation current envelope defining a first series of pulses occurring at a frequency F1 and having a pulse width PW1, and defining a second series of pulses occurring at frequency F2 and having a pulse width PW2.

Turning now to FIG. 3, another exemplary embodiment of a stimulation current is illustrated in which the original carrier waveform shown in FIG. 1 has been amplitude modulated such that a first and a second series of pulses are defined by the stimulation current envelope, the first series of pulses having a frequency F1 and a pulse width PW1, and the second series of pulses having a frequency F2 and a pulse width PW2. It may be seen that in this embodiment, the second series of pulses occur at a higher frequency (F2), have a shorter pulse width, and are of a lesser magnitude than the pulses within the first series of pulses. However, it may be seen that in other embodiments of stimulation currents, the pulses of one series of pulses may have higher or lower frequencies, shorter or longer pulse widths, and greater or lesser magnitudes than the pulses of another series of pulses, without departing from the scope and spirit of the presently contemplating disclosure. In this manner, it may be seen that such a stimulation current defining an envelope with multiple series pulses may be created. As a result, by optimizing the parameters of the pulses of each series of pulses, neural entrainment of certain neurons within the patient's brain may be facilitated at Frequencies F1 and/or F1 when the stimulation current is delivered to the patient, with the stimulating current still being charge balanced and not resulting in substantial patient discomfort. By, for example, configuring the stimulation current to have different pulse widths or amplitudes for certain of the series of pulses, it may be seen that certain types or regions of neurons may be targeted by some of the series of pulses for neural entrainment, while other types or regions of neurons may be targeted by others of the series of pulses for neural entrainment.

It may also be seen that other types of schemes for creating a combined stimulation current envelope having other features may be utilized, such as those in which the stimulation current is generated in which the stimulation current envelope defines three or more series of pulses, each series of pulses which may have different parameters in order to facilitate neural entrainment of different types of neurons, or in which the frequencies of the series of pulses defined by the stimulation current envelope are adjustable or configured to adjust according to the receipt of or other feedback, stimuli, or other inputs at the transcranial electrostimulation device.

According to certain exemplary embodiments, in particular it has been discovered that by administering a charge balanced stimulation current which contains a blend of different frequency patterns, neuronal responses within a patient's brain may be evoked which may tend to result in metabolic cleansing and regeneration in damaged neurons. Notably, it is contemplated that administration of a charged balanced stimulation current having a stimulation current envelope that defines a first series of pulses occurring at certain frequencies between 4 Hz and 100 Hz, when delivered to the patient, may tend to evoke a metabolic cleansing response. The particular frequency chosen may differ depending on the particular characteristics of, among other things, the neurons targeted for treatment, the region of the neurons within the patient's nervous system, the particulars of the underlying clinical conditions of the patient, and possible the individual characteristics and needs of the patient. For example, it has been found that in some circumstances, the frequency may be delivered at 4 Hz to achieve a beneficial result. It has also been discovered that a stimulation current having an envelope which defines a series of pulses occurring at a 40 Hz frequency, when delivered to the patient, may tend to promote beneficial results, such as a neuronal regenerative response. Thus, it is contemplated that a stimulation current having a stimulation current envelope that defines both a 4 Hz first series of pulses and a 40 Hz second series of pulses may be delivered to a patient in order to achieve both of these results simultaneously. Further, it is contemplated that by varying the frequency least one of the two series of pulses over time during the administration of a treatment regimen, a synergistic beneficial effect may be realized as a result of the different neural entrainment outcomes resulting from the particular choices used. For example, in one particular embodiment, the stimulation current may have a stimulation current envelope defining a first series of pulses occurring at a constant 40 Hz frequency for the entire duration of the treatment, with the stimulation current envelope also defining a second series of pulses occurring at a variable frequency, the variable frequency being 4 Hz for a first portion of the treatment, 40 Hz for a second portion of the treatment, and 77.5 Hz for a third portion of the treatment. It is further contemplated that for a treatment with a duration of an hour, each of the first, second, and third portions of treatment may be roughly equal, i.e. be 20 minutes in length. As such, the electrostimulation device may be configured to output a stimulation current according to these parameters. It may also be seen that via the delivery of a stimulation current having different frequency and amplitude patterns characteristics of its combined stimulation current envelope, multiple different neural regions may be configured to be stimulated in various ways across a single course of treatment, according to the effects desired to be achieved via such stimulation treatment regimens.

Figure 4:
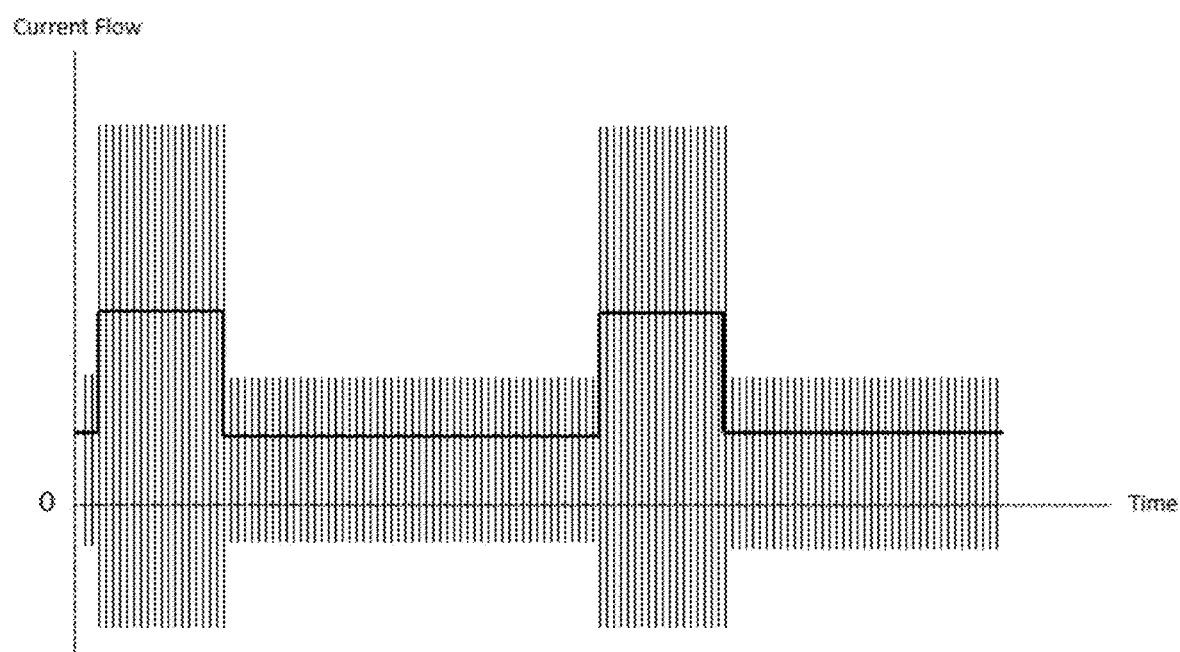
FIG. 4 is an illustration showing an example of a resultant rectified charge that is entrained at the neurons within the frontal cortex region of a patient's brain, overlaid atop the example of the stimulation current shown in FIG. 2, the resultant rectified charge occurring as a consequence of transcranial application of the illustrated stimulation current to frontal cortex region of a patient's brain.

Turning now to FIG. 4, an example of a resultant rectified charge that is entrained at the neurons within the frontal cortex region of a patient's brain as a result of delivery of an exemplary stimulation current to the frontal cortex region of the patient's brain is shown overlaid atop that exemplary stimulation current. It may be seen that this resultant rectified charge may occur as a consequence of application of the illustrated stimulation current to frontal cortex region of a patient's brain, which causes this rectified charge to accrue at the neurons. This rectified charge accrual results in polarization of the electrical charge on the outside of the neural membrane, in accordance with the frequency of the first series of pulses defined by the envelope of the stimulation current. As long as the magnitude and pulse width of the pulses defined by the stimulation current envelope are sufficient to cause sufficient accrual of electrical charge at a neuron to elevate the resting potential of the neuron to the threshold of excitation, an action potential of the neuron will be triggered. As may be seen, a higher magnitude pulse of a lesser pulse width may be sufficient to cause enough charge to accrue, or a lower magnitude pule of a greater pulse width may be sufficient, so long as the sufficient voltage is achieved at the membrane of the neuron as a result of delivery of the stimulation current. Further, it may be seen that so long as the frequency of the series of pulses are not too high (i.e. longer than the neuronal refractory period) each pulse will separate trigger another action potential within the neuron in order to cause natural entrainment to the frequency of the first series pulses. It may further be seen, however, that configurations of the different parameters of stimulation currents may result in some pulses being received at some neurons prior to the recovery of the neuronal refractory period resulting from triggering of the action potential by an earlier pulse. Such schemes may be utilized in order to, for example, target entrainment of certain types or localities of neurons according to a first frequency, and to target entrainment of another type or locality of neurons according to a second frequency.

It may further be seen that the electrostimulation current as presently contemplated may be delivered to the frontal cortex of the patient via different methods, or combinations of methods. For example, transcranial methods whereby the electrostimulation current is delivered to the frontal cortex via conduction between electrodes through soft tissue and skull, where a portion of the current penetrates the scalp and is conducted through the brain. However, it may be seen that delivery of the electrostimulation current to the frontal cortex may be achieved in other ways, such as via transcutaneous delivery of the stimulation current between the electrodes, whereby one or more nerves which are efferent to the frontal cortex, or regions thereof, are affected by the stimulation current, thereby resulting in a propagation of the pulses of the stimulation current by the targeted nerves to the frontal cortex, and thus entrainment at the efferent destination of the targeted nerves. In this manner, it may be seen that transcranial and transcutaneous current delivery may be alternate methods to achieve the result in the entrainment of neurons at the frontal cortex or locations within, and further, that such methods may be used in combination with each other to potentially yield further beneficial effects.

Figure 5:
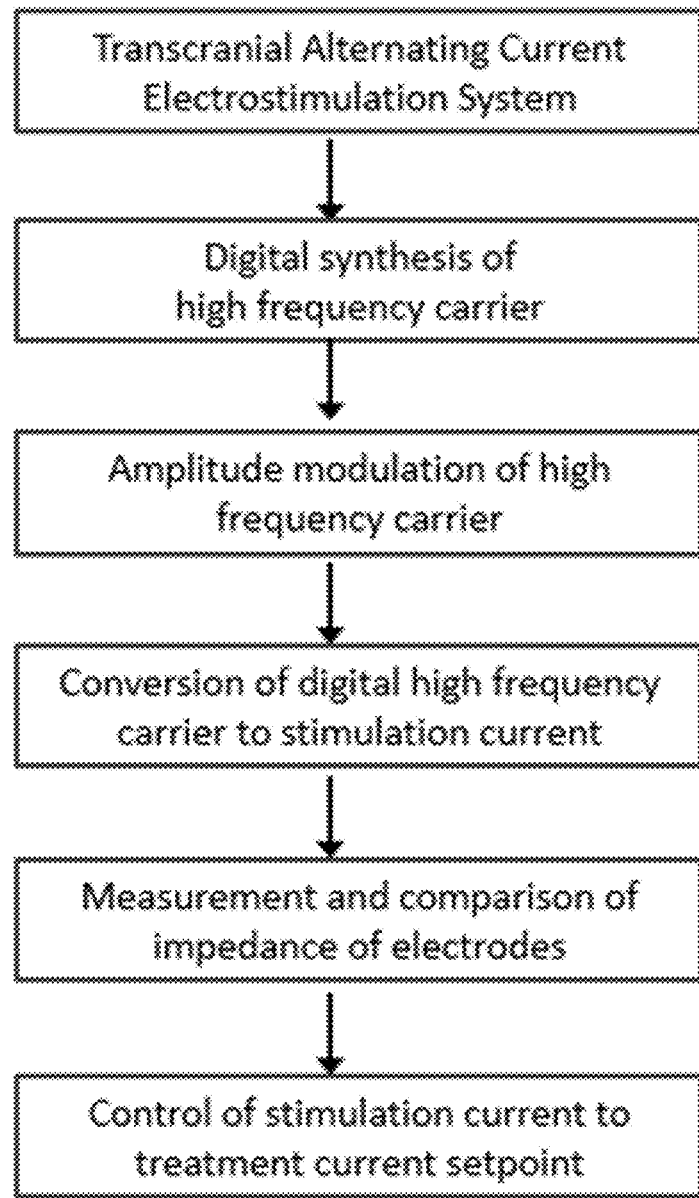
FIG. 5 is a flowchart showing certain steps of an embodiment of a method for treating a patient for anxiety, depression, and insomnia.

Turning now to FIG. 5, a flowchart showing certain steps of an embodiment of a method for treating a patient for anxiety, depression, and insomnia via the dynamic delivering a charge balanced alternating current electrical signal to the frontal cortex region of a patient's brain is shown. In particular, it is contemplated that a TCES system may first digitally synthesize one or more high frequency rectangular AC carrier waveforms, which may or may not be similar to the waveform illustrated in FIG. 1. The TCES system may then amplitude modulate the high frequency carrier waveform, as described in detail above, according to the particular parameters ultimately desired in the stimulation current, ultimately producing a stimulation current, which will then be conveyed to the patient. It is further contemplated that in certain embodiments, a measurement of electrode contact impedance may be taken at the patient at the point of delivery of the stimulation current via one or more reference electrodes. In these embodiments, the stimulation current may then be controlled (such as via alternation of the parameters of the high frequency carrier waveform, or by alteration of the various factors of the amplitude modulation) in order to better optimize the performance of the stimulation current, to confirm electrode contact quality, and to prevent any current imbalances that may result in unequal stimulation or inadvertent generation of DC components that may result in discomfort to the patient.

Figure 6:
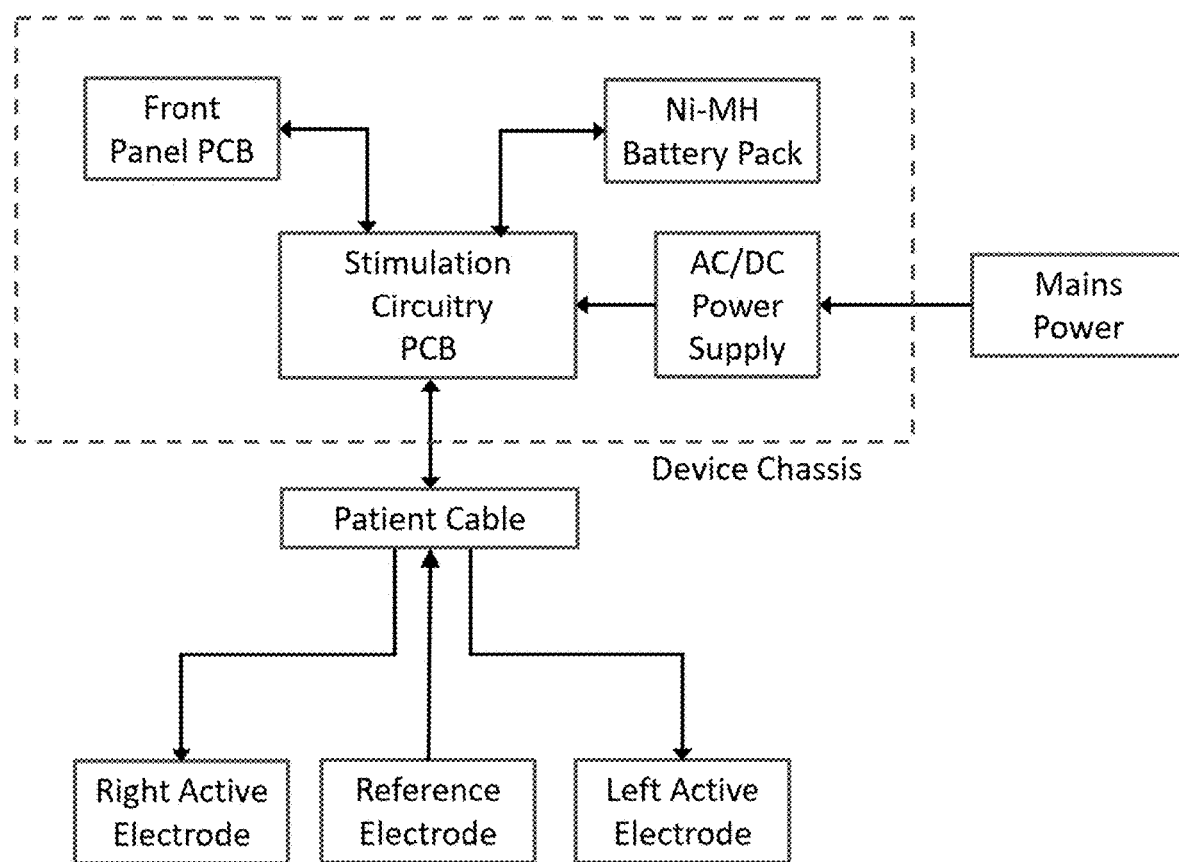
FIG. 6 is a block diagram showing certain hardware components of an embodiment of a electrostimulation system for treating a patient for anxiety, depression, and insomnia.

Turning now to FIG. 6, a block diagram of an exemplary Transcranial Alternating Current Dynamic Frequency Stimulation (tACS) system is illustrated. As may be seen, one exemplary embodiment of a tACS system may comprise a device chassis containing an AC/DC power supply, a stimulation circuitry printed circuit board (PCB), a front panel PCB, and a battery pack, configured for use with an external mains power source that feeds into the AC/DC power supply. Also included is a patient cable for conveying the stimulation current to the patient may be attached to the stimulation circuitry PCB, with the patient cable having a right active electrode, a left active electrode, and a reference electrode. While this specific block diagram shows one exemplary version of a tACS system, it is certainly not the only configuration in which the systems and methods herein described may be achieved, and indeed, these descriptions of the actual physical architecture of a tACS system are to be understood as being purely for exemplary purposes in order to enable the reader to more fully understand the nature of the herein described systems and methods, and are not to be interpreted as representing or imposing any limitations of the subject matter described herein. For example, but without limitation, it may not be necessary for some or all components to be contained within a physical device chassis, or for many of these components to be present in the exact form described or at all.

The stimulation circuitry PCB may be for controlling the functionality of the tACS related to the generation and control of the stimulation current, including the synthesis of a high frequency carrier waveform. In this respect, it is to be understood as including as subsidiary components (which may be hardware or software components, or combinations thereof) both the waveform generator and the stimulation current generator. The stimulation circuitry PCB will be more fully described in relation to the foregoing discussion of FIG. 7.

The front panel PCB may be for supporting the user interface for the tACS system, and may include, for example, means for user input and for display of information to the user. The front panel PCB will be more fully described in relation to the foregoing discussion of FIG. 8.

The patient cable may be for conveying the stimulation current produced at the tACS to the patient. The patient cable may include or be connected to two or more active electrodes for delivering the stimulation current to the patient, and may further include or be connected to one or more reference electrodes for determining stimulation output voltage and returning measurements which will be used to determine electrode impedance. The active electrodes may comprise a pliable substrate with an electrically conductive adhesive. In an exemplary embodiment, the active electrodes may be applied to the left and right mastoid region of the patient, with the reference electrode applied to the patient's forehead. However, it may be seen that in other configuration which may be optimized for other types of stimulation, the location, positioning, quantity, etc. of the active electrodes and the reference electrode(s) may be different.

The power supply, which in the exemplary embodiment may be optional and which may be a medical grade AC/DC power supply, may be any power supply or other which may be used to receive mains power and to permit that mains power to be conveyed the remainder of the system and utilized to ultimately produce a stimulation current. Likewise, the battery pack, which again may be an optional component, and which in the exemplary embodiment is a Ni-MH battery pack that also includes a battery management system, may serve to provide uninterrupted power during mains power failure, and which may serve to prevent artifact generation (spikes, jitters, etc.) that may occur during failure or intermittent losses or reduction in mains power delivery, as such artifacts may be included within the stimulation current which may result in inadvertent rectification of the stimulation by the skin and production of a DC current component, leading to patient discomfort. However, it may be seen that the presence or absence of these components are not of critical importance to the systems or methods herein disclosed, and that, such systems or methods may be performed without a battery pack or a power supply, so long as the mains power or other source of current used to produce the stimulation current is sufficient to enable performance of the herein discussed methods.

Figure 7:
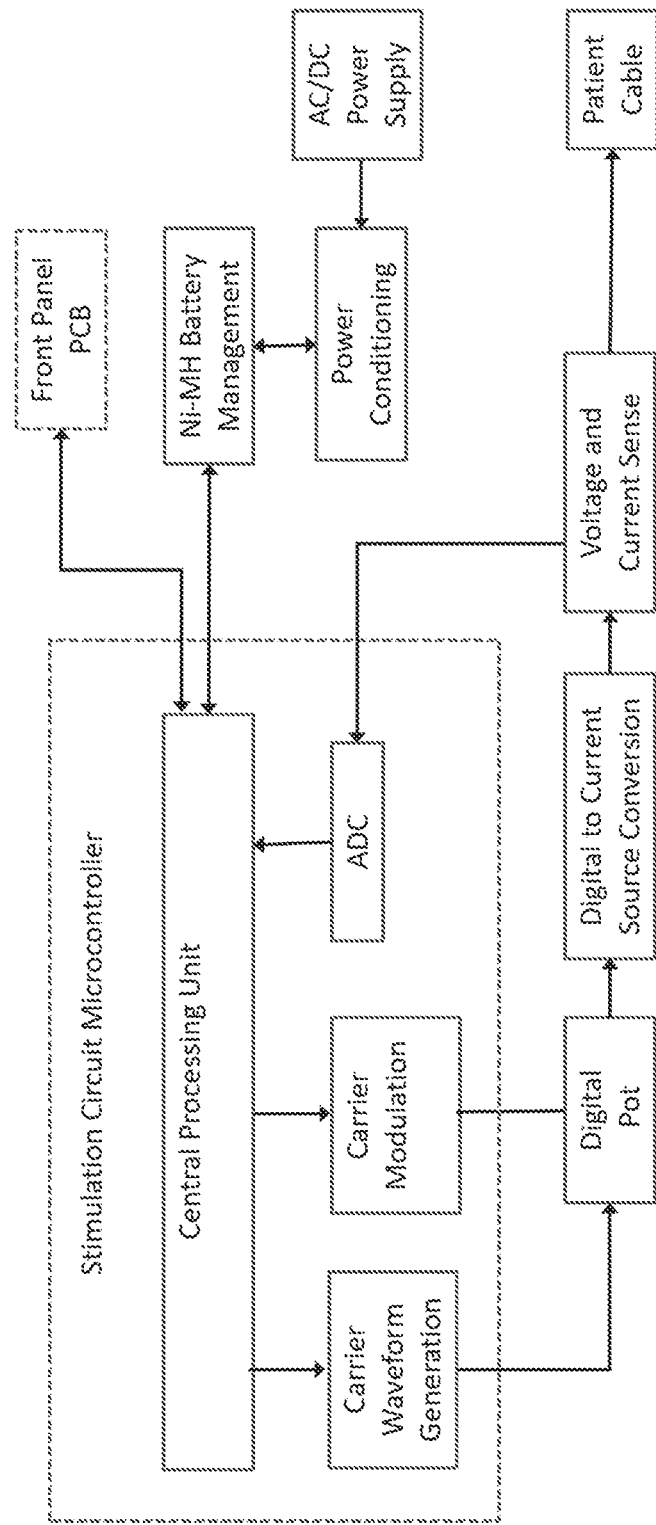
FIG. 7 is a block diagram showing, in greater detail, certain hardware and/or software components of a stimulation circuitry PCB included in one embodiment of a transcranial electrostimulation system for treating a patient for anxiety, depression, and insomnia.

Turning now to FIG. 7, a block diagram showing, in greater detail, certain hardware and/or software components of a stimulation circuitry PCB according to one embodiment of a transcranial electrostimulation system for treating a patient for anxiety, depression, and insomnia. As may be seen, the stimulation circuity PCB may, in the exemplary embodiment shown, include a stimulation circuit microcontroller comprising a central processing unit (CPU), a waveform generator module, a waveform modulation module, and an analog to digital converter (ADC) module, with the stimulation circuity PBC also including a digital to current source converter module, a voltage and current sense module, a digital potentiometer (pot), a Ni-MH battery management module, a power conditioning module, and inputs/outputs to the front panel PCB and to the patient cable. While this specific block diagram shows one exemplary version of the stimulation circuitry of a tACS system, it is certainly not the only configuration in which the systems and methods herein described may be achieved, and indeed, these descriptions of the physical and/or digital architecture of the stimulation circuitry of a tACS system are to be understood as being purely for exemplary purposes in order to enable the reader to more fully understand the nature of the herein described systems and methods, and are not to be interpreted as representing or imposing any limitations of the subject matter described herein. It is also to be understood that the respective modules described herein may be implemented in hardware, in software, or in combinations of hardware and software, including as subsidiary components of one another or integrated together.

The CPU may provide software control of all hardware functions in the tACS system. The CPU may also receive inputs from the ADC module and perform calculations based upon those inputs in order to control the functionality of the tACS system and its subordinate components in real time.

The carrier waveform generator module may be controlled by the CPU and may generate a carrier waveform according to the specific parameters desired, which may include a duty cycle and current amplitude ratio. The carrier waveform may then be then amplitude modulated with a carrier waveform via a digital potentiometer controlled by a waveform modulation model (also potentially controlled by the CPU) to perform the herein described steps in order to produce a digital representation of the herein described stimulation current. According to a preferred embodiment, the carrier waveform and thus the resulting stimulation current has a frequency of about 100 KHz.

Following amplitude modulation of the carrier waveform, a digital to current source converter, i.e. the stimulation current generator, may be used to ultimately generate, from a digital representation of the amplitude modulated carrier waveform, the actual stimulation current for subsequent delivery to the patient. According to a preferred embodiment, the stimulation current is about 15 mA. However, it may be seen that the stimulation current flow may also be at different rates.

The ADC module may be configured to receive analog information from a voltage and current sense module and to convert that analog information to digital information for use by the CPU in order to permit real-time adjustment of the stimulation current. Such analog information may be, according to certain contemplated embodiments, information received from an active electrode or a reference electrode, which may concern quality of electrode contact, electrical impedance, etc. Such information may be used to provide feedback to the CPU and to permit dynamic adjudgments to be made in real time to the stimulation current, such as via adjustment of the underlying waveform, the modulation signal(s), or directly at the stimulation current itself.

In the exemplary embodiment, a power conditioning module may also be included within or in relation to the stimulation circuitry PCB for regulating the power supply to voltage supply rails for the operation of the microcontroller and the stimulation output circuitry.

Figure 8:
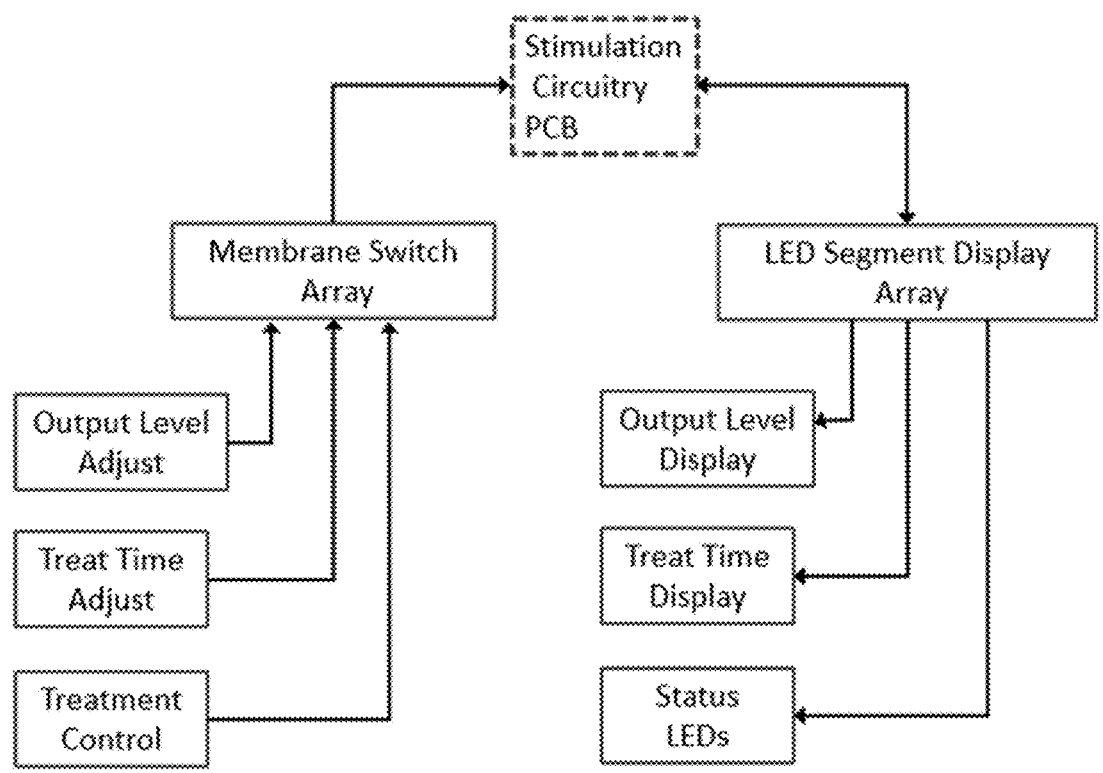
FIG. 8 is a block diagram showing certain hardware and/or software components of a front panel of an embodiment of an electrostimulation system for treating a patient for anxiety, depression, and insomnia.

Turning now to FIG. 8, a block diagram is illustrated that shows certain hardware and/or software components of a front panel of an exemplary embodiment of a transcranial electrostimulation system for treating a patient for anxiety, depression, and insomnia. In this exemplary embodiment, the front panel may be seen to include a membrane array switch and a LED segment display array. The membrane array switch may be utilized by the user of the TECS system in order to manually input adjustments to the parameters of the stimulation current, such as output level, treatment time, or treatment controls. The LED segment display array may be viewed by the user to visually confirm these parameters and the overall status of the device. It is to be understood that a this description of a front panel is purely illustrative in nature and is specific to one exemplary embodiment of a TECS system, and that the presence, absence, or specific configuration of any front panel, or any panel located anywhere on any such device, or the controls or displays contained therein, are purely illustrative of merely one particular embodiment, and these descriptions are certainly not meant to impose any limitations on the inventive aspects of the herein described systems and methods.

Figure 9:
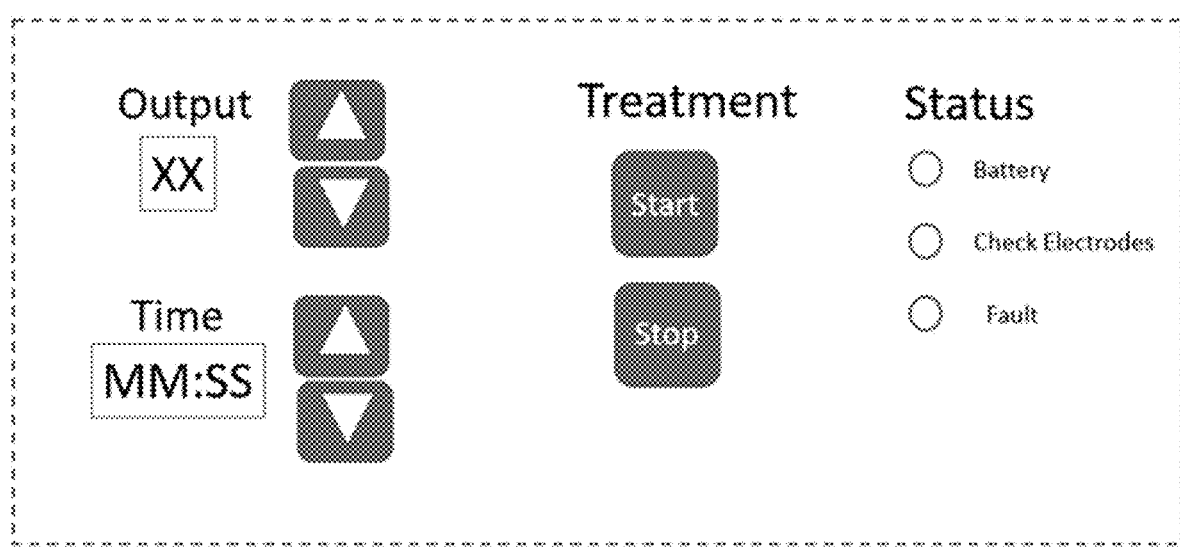
FIG. 9 is an exemplary image of a front panel user interface of an embodiment of an electrostimulation system for treating a patient for anxiety, depression, and insomnia.

Turning now to FIG. 9, an exemplary image of a front panel user interface of an embodiment of a transcranial electrostimulation system for treating a patient for anxiety, depression, and insomnia is shown. It may be seen that the front panel user interface may, according to the particular embodiment illustrated, include controls from adjusting an output, which may be a current level setpoint (i.e. in milliamperes) or even an alphanumeric signifier that relates to a treatment type, such as the output of a stimulation current according to one of the many aforementioned variations in frequency or multiple frequencies, or an entire set of predefined treatment parameters encompassed within a treatment modality. A treatment time may also be adjusted, as well as a manual start/stop button for beginning or ending the treatment. The front panel user interface may also contain, without limitation, one or more status LEDs for indicating a status condition, such as a battery status (i.e., fully charged, low charge, no charge remaining, etc.), a check electrode status (i.e. no or poor contact of one or more electrodes), or a general fault status which may indicate other conditions not encompassed by other status indicators. However, it is to be understood that a this description of a front panel user interface is purely illustrative in nature and is specific to one exemplary embodiment of a TECS system, and that the presence, absence, or specific configuration of any front panel user interface, or the controls or displays contained thereon or therein, are purely illustrative of merely one particular embodiment, and these descriptions are certainly not meant to impose any limitations on the inventive aspects of the herein described systems and methods.

Clinical Trials

Trial 1—Treatment of Insomnia Disorders: A randomized, double-blind, blank controlled trial of transcranial alternating current stimulation in the treatment of insomnia disorders was conducted in two hospitals in China using the Nexalin ADI tACS device. There were a total of 124 subjects in this trial. After 20 treatments (40 minutes/time) of each insomnia patient with the Nexalin ADI device, the effect of improving sleep was obvious, and there were no known adverse reactions. At the end of the 4-week follow-up period, sleep still improved significantly, and there were no known adverse reactions.

Trial 2—Treatment of Depression (Combined Medication):

tACS therapy using the Nexalin ADI tACS device was used to treat 124 patients with depression. Subjects were recruited who have never taken antidepressants before, and small doses of antidepressants were added when they were enrolled. 10 mg/day of Fluose fine hydrochloride was administered to each patient. After 20 treatments (40 minutes/time) with the tACS device, the overall severity of depression and the severity of factors such as anxiety somatization, weight, cognitive impairment, block, and sleep disorders were significantly improved; while treating the depressed patient population accompanied by Anxiety symptoms, including mental anxiety and physical anxiety, have obvious curative effects, and there were no known adverse reactions. At the end of the 4-week follow-up period, the effect of treating depression was still improved significantly, and there were no known adverse reactions.

Conclusion: NEXALIN ADI transcranial alternating current therapy technology is suitable for treating patients with depression disorder, especially those with anxiety symptoms, with obvious curative effect and no obvious adverse reactions.

Trial 3—Treatment of Depression (Pilot Study, No Combined Medication):

tACS therapy using the Nexalin ADI tACS device was used to treat 30 patients with depression. Patients were recruited who have never taken antidepressants before. After 4 weeks of Nexalin ADI device treatments, the remission ratio of the active group was higher than the sham group. In addition, the remission ratio in the 4th week was higher than that in the 8th week, indicating that the acute effect of tACS in reducing the degree of depression was obvious. After the treatment, at the 8th week of follow-up, the patient's depression level rebounded to a certain extent, but the antidepressant effect was still obvious, which proved that the effect of Nexalin ADI can last until the 8th week. It was concluded that tACS had the effect of reducing depression, with no observed adverse reactions.

Trial 4—Treatment of Depression (Full Study, No Combined Medication):

tACS therapy using the Nexalin ADI tACS device was used to treat adult patients major depressive disorder (MDD). 100 patients with first-episode, drug-naïve MDD were recruited and randomly assigned to receive 40-minute, 77.5 Hz, 15 mA, active or sham tACS (n=50 for each group) 5 days a week for 4 consecutive weeks, followed up by an additional 4-week efficacy/safety assessment without tACS treatment (week 8). The primary outcome was a remission rate defined as the 17-item Hamilton Depression Rating Scale (HDRS-17) score ≤7 at week 8. Secondary analyses were response rates, changes in HDRS-17 from baseline to week 4 and week 8, and rates of adverse events. Data were analyzed in an intention-to-treat sample. Forty-nine in the active and 46 in the sham completed the study. Twenty-seven of 50 (54%) in the active treatment group and 9 of 50 (18%) in the sham group achieved remission at the end of week 8. The remission rate was significantly higher in the active group compared to that in the sham group with a risk ratio of 1.78 (95% CI, 1.29, 2.47). Compared with the sham, the active group had a significantly higher remission rate at week 4, response rates at week 4 and week 8, and a larger reduction in depressive symptoms from baseline to week 4 and week 8. Adverse events were similar between the groups. The results suggest that tACS on the frontal cortex and two mastoids is effective and safe for patients with first-episode drug-naïve depression in an outpatient setting.

Inclusion Criteria: 1) 18-65 years old, Han Chinese; 2) met the diagnostic criteria of unipolar, non-psychotic MDD according to the Diagnostic and Statistical Manual of Mental Disorders, $4^{th}$ edition., text revision (DSM-IV-TR)[26]; 3) the 17-item Hamilton Depression Rating Scale (HDRS-17) total score higher than 17 points at baseline; 4) acute episode; and 5) no prior psychoactive drug treatment.

Exclusion Criteria: 1) a current or history of comorbid Axis I psychiatric disorders (including hypomanic or manic episode, panic disorder, agoraphobia, social phobia, obsessive-compulsive disorder, posttraumatic stress disorder, psychotic disorder, anorexia nervosa, bulimia nervosa, generalized anxiety disorder) and antisocial personality disorder in Axis II as assessed via the Mini-International Neuropsychiatric Interview (MINI) Chinese version $5.0^{27}$; 2) a current or history of organic brain disorders or neurological disorders; 3) acute suicidal risk as shown by a score of 3 or 4 on the suicide item of HDRS-17; 4) prior exposure to electroconvulsive therapy (ECT), modified electroconvulsive therapy (MECT), TMS, tDCS, tACS, or other neurostimulation treatments; 5) cochlear implant, cardiac pacemaker, and implanted device or metal in the brain; 6) prior or current psychotropic treatment; 7) prior or current any psychotherapy; 8) pregnant or lactating; 9) participation in a concurrent clinical trial; 10) refusal to sign informed consent to participate in the trial.

The criteria for excluding participants as failing to complete the trial were: 1) missed two consecutive tACS sessions due to any reason; 2) severe adverse events; 3) any medication treatment that may affect mood changes; 4) unable to complete on-site assessments at week 4 and at week 8.

Study Procedures: Participants were prescreened via brief face to face unstructured interviews and those who met the general criteria were invited for additional on-site screening. According to DSM-IV-TR, all participants were confirmed on MINI to suffer from the current episode of major depression. The reliability and validity of the MINI Chinese version 5.0 are consistent with the English version. At the baseline visit, demographic and clinical data were collected, including age, sex, marital status, the highest level of education, occupation, body mass index (BMI), disease duration, family history of depression, substance use, and medical histories including neurologic disorder, psychiatric disorder, and traumatic brain injury. Depressive symptoms were assessed at baseline, week 4, and week 8 by HDRS-17 and the Clinical Global Impression scale (CGI).

The Chinese version of HDRS-17 has been validated with psychometric properties. The CGI includes the severity scale (CGI-S) and the improvement scale (CGI-I), both of which are 7-point rated scales. AEs were recorded at week 4 and week 8. The frequency and severity of treatment-emergent adverse events were assessed with a self-reported common adverse effects questionnaire that includes 18 items. To monitor manic/hypomanic symptoms during the study, the Young Mania Rating Scale (YMRS) was administered at baseline, week 4, and week 8.

Upon the request of the local ethics committee, two EEG technicians recorded for at least 30 minutes on a 23-channel electroencephalogram (EEG) according to the International 10/20 system of electrode placement before the first stimulation, after the 4-week stimulation, and at the end of week 8 for safety. The EEG technicians were blinded to the treatment arm. For those patients with epileptiform activities before stimulation, they were excluded from the study. For those patients who showed epileptiform activities after randomization and 4 weeks of treatment, the principal investigator and an EEG technician conducted a re-evaluation of the EEG. For those patients who continued to exhibit epileptiform activities, a thorough evaluation of epileptic seizures, including EEG and brain imaging was provided.

Randomization, Concealment, and Blinding: Investigators randomly assigned eligible participants to receive active or sham tACS with a ratio of 1:1 according to a computer-generated list of random numbers. An independent statistician prepared a randomization sequence with a block size of 4. Before the first treatment, the nurse assigned each participant a number by opening an opaque, sealed envelope with the corresponding code for group allocation, and fixed it to the same tACS device during the 4-week tACS treatment phase. The statistician also coded the tACS device. All the instruments applied in the study were the same in size, color, appearance, weight, and odor. The other two devices (1 sham and 1 active) were available as a backup if any other devices did not work. At the end of the study, blindness was evaluated by separately asking participants and raters to determine which group they were randomly assigned to. All study staff (including investigators, nurses, EEG technicians, and raters) and patients were blinded to the group allocation.

tACS Intervention: Participants sat comfortably on reclining chairs to receive FDA-approved tACS (Nexalin Technology, Inc., Houston, TX, USA), which was administered by trained nurses in accordance with standardized instructions. Patients were advised to relax, drink water, or even sleep, with minimal communication with the nurses. Three Nexalin electrodes were placed overhead. In the 10/20 international placement system, a 4.45 cm×9.53 cm electrode was placed on the forehead corresponding to Fpz, Fp1, and Fp2. Two 3.18 cm×3.81 cm electrodes were placed on the mastoid region of each side. The tACS stimulation waveform includes ramp-up and ramp-down periods of 180 and 12 seconds, respectively. It was a square-wave with an average amplitude of 15 mA and was equally distributed from the frontal region to the mastoid areas (amplitudes are reported as zero-to-peak).

All participants were treated for a total of 20 sessions with stimulation at 77.5 Hz and 15 mA. Sham tACS had no active stimulation. From Monday to Friday, each session lasted 40 minutes at a fixed daytime interval. During the entire intervention period, each participant was assigned to the same tACS device regardless of active or sham.

Outcomes: Trained investigators and raters were blind to the participants' assignments and performed the assessments. Efficacy and safety were evaluated at baseline, week 4, and week 8. The primary outcome was the rate of clinical remission, defined as the HDRS-17 total score ≤7 at week 8. The secondary outcomes were: 1) the remission rate at week 4; 2) rates of response defined as a ≥50% reduction in HDRS-17 total score from baseline to week 4 and week 8; 3) change of HDRS-17 score and its subscales from baseline to week 4 and week 8; 4) changes from baseline to week 4 and week 8 in CGI-S and CGI-I scores; 5) incidence of AEs, including treatment-emergent adverse events, YMRS (manic or hypomanic episode defined as YMRS score >8), and epileptiform activities revealed by EEG recordings.

Statistical Analyses: The sample size was estimated with a power of 80% and a 2-tailed α level of 5%. According to an early pilot study of tACS in treating adult patients with drug-naïve MDD, it was found that the remission rates at the end of the 8-week study period in the active and sham groups were 50% and 20%, respectively. Thus, the minimum sample size required for each group was 39. Considering the attrition rate of 20% and a block size of 4, each group required 50 participants, with a total sample size of 100. Data were analyzed in the intention-to-treat (ITT) sample with worst-case imputation.

Regarding binary outcomes, the relative risk (RR) and risk difference (RD) were calculated to compare the relative and absolute benefits between the active and sham groups. The HDRS-17 total score and other continuous variables were expressed as the mean difference (MD) with 95% confidence interval (CI). The baseline characteristics between the two groups were compared using $\chi^2$ tests or Fisher exact tests for categorical variables, and Mann-Whitney U tests for continuous variables. A logistic regression analyses was performed to evaluate the treatment efficacy of the primary outcome. For the secondary analyses, general linear model and logistic regression were used for continuous and binary outcomes. The linear mixed-effects model (LMMs) was used to evaluate the differences in symptom changes between the two groups at week 4 or week 8, including the interaction between group (active versus sham) and time (baseline, week 4, and week 8). All hypotheses were tested at a significance level of 0.05, using unpaired, 2-tailed tests. SAS, version 9.4 (SAS Institute Inc) was used.

Results:

Baseline Characteristics of Participants: A total of 168 individuals were screened and 68 were excluded for different reasons. Of those excluded from the study, 48 did not meet inclusion criteria, 6 refused to participate in the study, 8 had active suicidal ideation or plan, and 6 were taking psychiatric treatment. A total of 100 first-episode, drug-naïve adult patients were included in the study and randomized 1:1 into two groups. During the treatment phase, four in the sham group and one in the active group dropped out. Thus, 49 in the active tACS group and 46 in the sham group completed the entire trial. No significant differences were found between the two groups.

Clinical Outcomes: For the primary analysis (n=100), there was a significant difference in remission rate between active (54.0%) and sham (18.0%) treatment, with a RR of 1.78 (95% CI, 1.29, 2.47) and a RD of 0.36 (95% CI, 0.19, 0.53). At week 4, 31 (62.0%) in the active treatment group achieved remission compared to 13 (26.0%) in the sham treatment group (RR, 1.95; 95% CI, 1.32, 2.88; RD, 0.36; 95% CI, 0.07, 0.45). At week 4, 35 (70%) participants in the active group and 21 (42%) in the sham group showed responses (RR, 2.63; 95% CI, 1.29, 5.36; RD, 0.28; 95% CI, 0.09, 0.47). Similarly, at week 8, 37 (74%) subjects in the active group and 19 subjects (38%) in the sham group responded (RR, 3.00; 95% CI, 1.40, 6.42; RD, 0.36; 95% CI, 0.18, 0.54).

The reduction in HDRS-17 total score at week 4 and week 8 in the active group was significantly greater than that in the sham group with MDs of −6.81 points (95% CI, −9.53, −4.09) and −6.35 (95% CI, −9.21, −3.49), respectively ($p_{interaction}$<0.01). In terms of subscale scores, all subscale scores in the active group except for genital symptoms and suicide scores were significantly lower than those in the sham group. In the active group, 96% (48/50) of participants reported feeling "much" or "very much" clinical improvement, compared with 70% (35/50) of participants in the sham group (RR, 7.50; 95% CI, 1.81, 31.10). At week 8, 94% (47/50) of the active group was significantly higher than 20% (10/50) of the sham (RR, 13.33; 95% CI, 4.41, 40.29). Compared with the sham group, the active group had lower CGI-S scores at week 4 and week 8 (week 4: MD, −1.63; 95% CI, −2.20, −1.06; week 8: MD, −2.74; 95% CI, −3.25, −2.23; $p_{interaction}$<0.01).

AEs and Safety: Treatment-emergent adverse events did not differ significantly between the two groups (RR, 1.10; 95% CI, 0.93, 1.31; RD, 0.08; 95% CI, −0.06, 0.22). The most common nonserious adverse reactions included aurium tinnitus (4 active and 1 sham participants), tinnitus cerebri (2 active and 2 sham participants), discomfort (2 active and 1 sham participants), headache (1 active and 1 sham participants), and itches (1 active and 1 sham participants), which were not statistically significant between the two groups. These adverse reactions occurred during the first two to four sessions of tACS intervention and did not persist during the acute treatment phase. No hypomania or mania occurred during the study. No deaths, seizures, neurological complications, phosphene perception, or other serious adverse events were observed.

Integrity of Blinding: Seventeen of the 46 subjects in the sham group (37%) and 25 of 49 subjects in the active group (51%) correctly identified the allocation group ($\chi^2$=1.90, p=0.17). Meanwhile, the raters correctly identified 23 (50%) in the sham group and 27 (55%) in the active group ($\chi^2$=0.25, p=0.62). Neither the participants nor the researchers were able to guess their actual group beyond chance.

Discussion: It was found that the active tACS at the frequency of 77.5 Hz and current of 15 mA in first-episode drug-naïve MDD patients had better remission and response rates than the sham tACS. Compared with sham treatment, almost all depressive symptom domains of active treatment were significantly improved. Meanwhile, there was no significant difference in adverse events between the two groups.

The efficacy of tACS in treating depression may depend on different stimulation parameters, including frequency and current. The results of an earlier small study using tACS with a frequency of 10 Hz or 40 Hz and 2 mA current appeared to support this speculation. Moreover, tACS with a frequency of 10 Hz, but without 40 Hz was significantly better than sham in relieving depressive symptoms. In this study, tACS with a frequency of 77.5 Hz and an alternating current of 15mA replicated the results of our pilot study, in which active tACS was significantly superior to sham in alleviating depressive symptoms in patients with first-episode, drug-naïve MDD. Importantly, the current of 15 mA in this study was higher than that in previous reports. Not only does tACS have an alpha frequency of 10 Hz but also a gamma rhythm of 77.5 Hz can treat major depression, indicating that there are some specific alpha or gamma frequencies or other unknown frequencies that have a therapeutic effect on major depression. Although their exact mechanism of action remains unclear, it does not affect the clinical application of these stimulation protocols in depression. In addition, different stimulation regions may also play important roles in the effect of tACS intervention on depression. In literature, the frontal cortex, ear lobes, maxilla-occipital junction, mastoid processes or temples were often reported as different targeting brain regions when different devices were used to treat depression. Two studies reported that two electrodes on the left and right frontal regions plus a third return/reference electrode on the vertex and one electrode on the frontal region and two references on two mastoid region also showed potential efficacy in reducing depressive symptoms. The other two studies with two electrodes on the bilateral temples or two electrodes on the two earlobes showed no significant difference between active and sham groups in reducing depressive symptoms. These data suggest that different electrode placements may produce antidepressant effects. However, it is necessary to conduct head-to-head comparison studies using the same or different stimulation parameters and/or different electrode positions to find the optimal location and stimulation parameters of tACS to treat depression.

Safety is a concern for the use of large current. However, most of the side effects of this study were mild. All these adverse events had been previously reported in tDCS (transcranial direct current stimulation) and tACS studies. More importantly, there was no prominent difference in adverse events between the two groups. Unlike tDCS, tACS did not cause hypomania or mania in this study, suggesting that tACS may be safer than tDCS. In addition, no aversiveness, phosphene perception, deaths, seizures, or other serious adverse events were reported in the study. The good concealment of the present study indicates that tACS is suitable for blind, sham-controlled studies, although mild perceptual skin sensations may occur.

In summary, this relatively large sample study confirmed that tACS had an antidepressant effect on depression within 8 weeks after 4 weeks, 5 days a week in patients with first-episode, drug-naïve MDD in a Chinese Han population. The tACS at a frequency of 77.5 Hz and a current of 15 mA was safe and well-tolerated, as well as did not cause confusion, which is one of the most common adverse reactions of ECT and MECT treating depression. The results of this study are the first step to provide evidence for the efficacy of tACS at 77.5 Hz frequency and 15 mA current targeting the frontal region and two mastoid regions in depressed patients.

The above description is given by way of example, and not limitation. Given the above disclosure, one skilled in the art could devise variations that are within the scope and spirit of the invention disclosed herein. Further, the various features of the embodiments disclosed herein can be used alone, or in varying combinations with each other and are not intended to be limited to the specific combination described herein. Thus, the scope of the claims is not to be limited by the exemplary embodiments.

It is also to be understood that the terminology employed in the Summary of the Invention and detailed description section of this application is for the purpose of describing particular embodiments. Unless the context clearly demonstrates otherwise, it is not intended to be limiting. In this specification and the appended claims, the singular forms of articles shall include plural references unless the context clearly dictates otherwise, and further, it is contemplated that any use of "and" or "or" statements shall be interpreted as interchangeable with one another. It is also contemplated that any optional feature of the variations described herein may be set forth and claimed independently or in combination with any one or more of the features described herein.

What is claimed is:

1. A method for treating a patient for anxiety, depression, and insomnia, the method comprising:
    (a) generating a stimulation current conveyed to the patient for a treatment duration via the steps of:
        generating a carrier waveform, the carrier waveform being an alternating current having a duty cycle ratio and a current amplitude ratio, the duty cycle ratio and the current amplitude ratio being selected such that each respective integration of the current amplitude between successive time instances at which the carrier waveform alternates polarity is substantially equivalent; and
        generating a stimulation current from the carrier waveform via amplitude modulating the carrier waveform, the extremes of the stimulation current defining a stimulation current envelope, the stimulation current envelope defining a first series of pulses occurring at a first frequency and a second series of pulses occurring at a second frequency, the first series of pulses occurring at a first frequency that does not substantially vary for the entire treatment duration, the second series of pulses occurring at a second frequency that varies during the treatment duration, the second series of pulses occur at a frequency between 4 Hz and 100 Hz; and
    (b) conveying the stimulation current to the frontal cortex region of the brain of the patient.

2. The method of claim 1, wherein the first series of pulses occur at a frequency between 4 Hz and 100 Hz.

3. The electrostimulation system of claim 1, wherein the treatment duration is about an hour, and wherein the second frequency varies during the treatment duration to predefined frequencies corresponding to a first portion having a duration of about 20 minutes, a second portion having a duration of about 20 minutes, and a third portion having a duration of about 20 minutes.

4. The method of claim 1, wherein in step (a), the stimulation current is generated via amplitude modulating the carrier waveform such that the stimulation current envelope defines a plurality of series of pulses, each respective one of the plurality of series of pulses occurring at a respective frequency.

5. The method of claim 4, wherein each of the plurality of stimulation current envelopes has a frequency between 4 Hz and 100 Hz.

6. The method of claim 1, wherein the carrier waveform has a frequency of about 100 KHz.

7. The method of claim 1, wherein the carrier waveform is a rectangular wave.

8. The method of claim 1, further comprising the steps of measuring the stimulation current at the patient and determining an electrode contact impedance therefrom, and based upon the determined electrode contact impedance, adjusting one or more parameters of one or more of: the carrier waveform output from the waveform generator, the stimulation current output from the stimulation current generator, or combinations thereof.

* * * * *